__United States Patent__ [19]

Kulla et al.

[11] Patent Number: 4,738,924

[45] Date of Patent: Apr. 19, 1988

[54] METHOD FOR THE PRODUCTION OF 6-HYDROXYNICOTINIC ACID

[75] Inventors: Hans Kulla; Pavel Lehky, both of Kanton Wallis, Switzerland

[73] Assignee: Lonza Ltd., Gampel, Switzerland

[21] Appl. No.: 29,684

[22] Filed: Mar. 24, 1987

Related U.S. Application Data

[63] Continuation of Ser. No. 703,518, Feb. 20, 1985, abandoned.

[30] Foreign Application Priority Data

Feb. 22, 1984 [CH] Switzerland .......................... 840/84

[51] Int. Cl.$^4$ ............................................ C12P 17/10
[52] U.S. Cl. .................................... 435/121; 435/117; 435/122; 435/131; 435/189; 435/190
[58] Field of Search ............... 435/117, 121, 122, 131, 435/189, 190, 253, 803, 824, 813

[56] References Cited

PUBLICATIONS

Briaucourt et al., J. Chim. Ther. (1973), 8, No. 2, pp. 226–232.
Allinson, M. J. C.—J. Biol. Chem. (1943), 147, pp. 785–791.
Behrman, E. J. and Stanier, R. Y.—J. Biol. Chem. (1957), 228, pp. 923–945.
Hunt, A. L.—Biochem. J. (1958), 72, pp. 1–7.
Ensign and Rittenberg—J. Biol. Chem. (1964), 239, pp. 2285–2291.
Hunt et al.—Biochem. Journal, vol. 69, pp. 170–173 (1958).
Hirschberg et al., Journal of Bacteriology, vol. 108, No. 2, pp. 751–756.

*Primary Examiner*—Margaret Moskowitz
*Attorney, Agent, or Firm*—Fisher, Christen & Sabol

[57] ABSTRACT

Process for the production of 6-hydroxynicotinic acid by biotechnological methods. Nicotinic acid is enzymatically hydroxylated in the presence of equivalent quantities of magnesium or barium ions with the help of nicotinic acid-hydroxylating microorganisms. The resultant magnesium or barium salt of the 6-hydroxynicotinic acid is separated from the reaction mixture. Then the 6-hydroxynicotinic acid is freed from the separated salts. Examples of the microorganism are the species Pseudomonas, Bacillus or Achromobacter, for example, *Achromobacter xylosoxydans*. Preferably the enzymatic hydroxylation is carried out at 20° to 40° C. and a pH of 5.5 to 9.0 under aerobic conditions.

9 Claims, No Drawings

METHOD FOR THE PRODUCTION OF 6-HYDROXYNICOTINIC ACID

This is a continuation of application Ser. No. 703,518, filed on Feb. 20, 1985, now abandoned.

BACKGROUND OF THE INVENTION

1. Field of the Invention

The invention relates to a process for the production of 6-hydrooxynicotinic acid by the biotechnical method.

2. Prior Art or Related Art

Several methods are known for the production of 6-hydroxynicotinic acid by means of organic syntheses. For example, 6-hydrooxynicotinic acid can be obtained from 2-pyridone by the Kolbe-Schmidt type carboxylation of hydroxy aromatics. Other syntheses start out from maleic acid or isocinchomeronic acid [Briaucourt et al., J. Chim. Ther. (1973), 8 (2) 226-32; Quarroz, Swiss Application No. 7731/80]. However, none of such synthesis permit a simple, inexpensive and favorable-to-the-environment type of production of pure 6-hydroxynicotinic acid. Such processes have the disadvantage that the conversion is not quantitative and undesirable by-products accompany the reaction. The by-products represent impurities which must be removed from the reaction product after reaction is completed.

It is also known that microorganisms of the variety *Bacillus, Pseudomonas, Clostridium, Sarcina* and *Mycobacterium* grow on nicotinic acid and that they use such substrate as a source of carbon, nitrogen and energy [Allison, M. J. C., J. Biol. Chem. (1943) 147, 785; Behrman, E. J., and Stanier, R. V., J. Biol. Chem. (1957) 228, 923]. In the case of all of such studied organisms, the nicotinic acid is oxidized to 6-hydroxynicotinic acid in the first decomposition step. The 6-hydroxynicotinic acid is further immediately converted, and without significant enrichment, in the case of aerobic organisms, to water, carbon dioxide and ammonia.

Only after break up of the microorganism, it is possible to isolate the nicotinic acid hydroxylase into more or less pure form [Hunt, A. L., Biochem. J. (1958) 72, 1-7]. The nicotinic acid hydroxylases are large molecules of approximately 400,000 dalton. They contain flavin cofactors, many metal atoms (Fe, Mo), inorganic sulfur and in some cases even selenium. The nicotinic acid hydroxylases are active only in the presence of suitable electron transmitting systems (for example, cytochrome, flavins, NADP+ and others). The nicotinic acid hydroxylase can be isolated from cell extracts and the enzyme preparations can be used for the hydroxylation of nicotinic acid. Such has been done and small quantities of 6-hydroxynicotinic acid were actually obtained [Behrman and Stanier, J. Biol. Chem. (1957) 228, 923]. Apart from the high costs of enzyme isolation and of the instability of the nicotinic acid hydroxylase, it was still necessary to take care of the regeneration of cofactors and electron transmitting systems.

In the case of many fermentations and enzyme reactions, the product concentration in the reaction solution are very low and, in the case of product isolation, it is necessary therefore to process large volumes of material. Such leads to high costs of processing, investment and sewage-treatment.

A similar situation also prevails in the case of the biotechnical production of 6-hydroxynicotinic acid (U.S. application Ser. No. 701,507, filed on Feb. 14, 1985). The enzymatic hydroxylation can be carried out with a 0.1 percent by weight up to a saturated nicotinic acid solution. The stability of the enzyme located in the cells, however, has been considerably lowered in the case of higher substrate concentrations. Therefore, the enzyme consumption and the enzyme costs also increase accordingly. On the other hand, the growth of microorganisms (Achromobacter) will be greatly impeded even in the case of relatively low nicotinic acid concentrations. The losses of enzyme could be compensated by slow growth of the cells during the reaction. Such, however, can happen only in the case of diluted nicotinic acid solutions (0.1 to 1.5 weight percent).

From the facts mentioned above, it would follow to the art that the enzymatic hydroxylation of nicotinic acid needs to be carried out in diluted solutions; such however leads to increased processing costs.

BROAD DESCRIPTION OF THE INVENTION

An object of the invention is to provide a process which overcomes the above-stated disadvantages of the prior art and mentioned related art. Another object of the invention and mentioned related art. Another object of the invention is to provide a process with which, in an economic manner, 6-hydroxynicotinic acid can be produced from nicotinic acid with very high purity and yield. Other objects and advantages are set out herein or are obvious herefrom to one skilled in the art.

The advantages and objects of the invention are achieved by the process of the invention.

This invention involves a process for the production of 6-hydroxynicotinic acid. The process includes enzymatically hydroxylating the nicotinic acid in the presence of equivalent quantities of magnesium or barium ions with the help of nicotinic acid-hydroxylating microorganisms. The resultant magnesium or barium salt of the 6-hydroxynicotinic acid is separated from the reaction mixture. Then the 6-hydroxynicotinic acid is freed from the separated salts.

In a preferred embodiment, a 0.1 weight percent up to a saturated solution of magnesium or barium salt of the nicotinic acid is used. The latter is inserted continuously into a suspension of an *Achromobacter xylosoxydans* held at a pH of 5 to 9 according to the measure of the enzymatic hydroxylation to the corresponding 6-hydroxynicotinic acid. The salts obtained of the 6-hydroxynicotinic acid are separated continuously.

The enzymatic hydroxylation preferably is carried out at a temperature of 10° to 50° C. Preferably the pH is held constantly at 5 to 9 by the addition of nicotinic acid. Also, preferably the reaction is carried out continuously. The microorganism used is preferably one of the species Bacillus, Pseudomonas or Achromobacter, and most preferably is *Achromobacter xylosoxydans* having the designation DSM 2783.

DETAILED DESCRIPTION OF THE INVENTION

As used herein, all parts, ratios, percentages and proportions are on a weight basis unless otherwise stated herein or otherwise obvious herefrom to one ordinarily skilled in the art.

Effectively, the bioreactor is filled with a 0.1 percent by weight of a saturated solution of a magnesium or barium nicotinate and then the cells rich in nicotinic acid hydroxylase are added. The magnesium or barium hydroxynicotinate forming during the reaction crystallizes out after reaching the limit of saturation. The reaction is carried out at temperatures of 10° to 50° C., perferably at 25° to 35°C. The pH value is kept constant at 5 to 9 by the addition of nicotinic acid.

A preferred method of operation of the invention is a continuous process according to which a 0.2 to 10 percent solution of magnesium or barium salt of the nicotinic acid is inserted into a suspension of an *Achromobacter xylosoxydans* held to a pH of 5 to 9 according to the measure of the enzymatic hydroxylation in relation to the corresponding 6-hydroxynicotinic acid. The magnesium or barium salts obtained of the 6-hydroxynicotinic acid are continuously separated.

The poor solubility of the magnesium or barium hydroxynicotinate makes it possible to allow the product to precipitate selectively during the reaction as magnesium or barium salt, the nicotinic acid remains in the solution. The magnesium or barium hydroxynicotinate forms fine microcrystals which can easily be separated by filtration or centrifuging. By acidification, it is possible to obtain pure 6-hydroxynicotinic acid from the salt.

The addition of the educt in the form of a solution of magnesium or barium nicotinate can take place automatically on the basis of the conductive capacity measurement by means of a pump coupled with the regulator. The crystals of the magnsium or barium hydroxynicotinate which are deposited on the bottom of the reaction vessel or in a built-in decanter can be periodically or continuously separated. Naturally, solid nicotinic acid can be introduced into the bioreactor together or parallel with a corresponding quantity of the magnesium oxide by means of a solid substance dosing device. Thus, one obtains a practically dosed system into which solid educt is introduced and a solid product is taken out. In this system one is able to operate with diluted substrate solution, that is, under conditions which guarantee a good enzyme stability without any problems of processing and sewage arising thereby.

The enzymatic hydroxylation is carried out by means of a microorganism as the nicotinic acid hydroxylase source.

It has been found that microorganisms of the varieties Pseudomonas, Bacillus and Achromobacter permit successful production of 6-hydroxynicotinic acid. Very effectively, *Achromobacter xylosoxydans* DMS 2402, (type strain), *Pseudomonas putida* KB1 NCIP 10521, NCIB 8176, or a Bacillus strain [which was described by Ensign and Rittenberg, J.Biol. Chem. 239, (1964) 2285–2291] is used. But preferably the new strain *Achromobacter xylosoxydans* DSM 2783 is used.

The taxonomic description (to the extend presently known) of the new strain *Achromonbacter xylosoxydans* DSM 2783 is as follows:

Name: *Achromobacter xylosoxydans* DSM No. 2783
Isolated from: nicotinic acid mother lye
(A) Morphology
  Cultivation in nutrient broth
  (1) cell shape: small rods 2 to 3.5μ long, approximately 0.6μ wide
  (2) arrangement: individually
  (3) motility: strongly movable; peritrically flagellated
  (4) endospore: none
  (5) gram: negative
  (6) oxidase: positive
  (7) catalase: positive
  (8) strictly aerobic Such new strain agress in all tested characteristics with the type strain of *Achromobacter xylosoxydans* DSM 2402, with the exception of hydrolysis of acetamide.

The cited strains of *Achromobacter xylosoxydans* are deposited at the German collection of microorgansims (DSM), Gesellschaft für Biotechnologische Forschung mbH., Griesebachstrasse 8, 4300 Göttingen, Federal Republic of Germany, under the numbers DSM 2402 and DSM 2783.

The new strain *Achromobacter xylosoxydans* DSM 2783 was deposited on Nov. 17, 1983, in the German collection of microorganisms (DSM), Deutsche Sammlung von Mikroorganism, Gesellschaft für Biotechnologische Forschung mbH., Griesebachstrasse 8, 4300 Göttingen, Federal Republic of Germany, under the designation or number DSM 2783. Such deposit of a culture of such new strain of microorgansim in such depository affords permanence of the deposit and ready accessibilty thereto by the public if a patent is granted, under conditions which assure (a) that access to the culture will be available during the pendency of the patent application to one determined by the Commissioner to be entitled thereto under 37 C.F.R. 1.14 and 35 U.S.C. 122, and (b) that all restrictions on the availability to the public of the culture so deposited will be irrevocably removed upon the granting of the patent. The applicants or their assigns have provided assurance of permanent availability of the culture to the public through such depository.

The strains *Pseudomonas putida* NCIP 10521 and 8176 can readily be obtained at the National Collection of Industrial Bacteria, Torry Research Station 135 Abbey Road, Aberdeen AB98DC, Scotland. The strain *Achromobacter xylosoxydans* DMS 2402 can readily be obtained at the above-mentioned West German depository.

The above-mentioned strains frow with nicotinic acid as the only source for carbon, nitrogen and energy. The cultivation of the above-named microorganisms can be accomplished according to the processes known for this type of strains. For example, strain DSM 2783 is fermented in a diluted and sterilized nicotinic acid solution (0.05 to 0.5 percent by weight), which contains phosphate buffer (50 mm) pH 7.0, trace elements in the following amounts (in mg/1):

$CaCl_2 2H_2O$: 20
$MnSO_4$.10
$FeSO_4.7H_2O$: 5
$CoCl_2.6H_2O$: 0.1
$CuSO_4.5H_2O$: 0.1
$ZnSO_4.7H_2O$: 0.1
$NaMoO_4 2H_2O$: 0.1

In order to accelerate the growth, such solution contains a small quantity of yeast extract (Merck) (0.05 percent by weight), for 24 to 48 hours at 30° C. under aerobic conditions. The grown biomass (approximately 10 g of moist weight/1) is rich in nicotinic acid hydroxylase. The cells are centrifuged off and can be used immediately or after storage at −20° C. directly, that is, to say without obtaining enzyme or purification, for the subject nicotinic acid hydroxylation. For carrying out the nicotinic acid hydroxylation, it is desirable that the decomposition of the nicotinic acid does not go beyond the first step, namely, the hydroxylation to 6-hydroxynicotinic acid. In this production phase, the growth of the microorganism would take place at the expense of the yield.

As mentioned above, the strain *Achromobacter xylosoxydans* DSM 2783 grows well in diluted nicotinic acid solution (0.05 to 0.5 weight percent) and completely consumes the given nicotinic acid at the same time. With rising concentration of the nicotinic acid, the cell growth is impeded and above 2 percent by weight of nicotinic acid concentration, no growth is observed any more. The activity of the nicotinic hydroxylase, however, remains unchanged in the cells. The catabolic decomposition is interrupted after the hydroxylation stage. Therefore, the side and secondary reactions are eliminated, and the purity and yield of 6-hydroxynicotinic acid are very high.

By way of summary, 6-hydroxynicotinic acid is produced by enzymatic hydroxylation from nicotinic acid in the presence of equivalent quantities of magnesium or barium ions with the help of a nicotinic acid-hydroxylating microorganism.

The practical use of the invention is shown by the following examples.

EXAMPLE 1

Production of *Achromobacter xylosoxydans* DSM 2783 cells

A nutrient solution which contained 51.9 g of $Na_2HPO_4 \cdot 2H_2$, 20.0 g of $KH_2PO_4$, 2.5 g of yeast extract and 10 g of nicotinic acid in 4750 ml of water was filled into the fermenter and was sterilized for 20 min. at 120° C. After cooling to 30° C., the fermenter was inoculated with 500 ml of the starter culture and was fermented at 30° C. and pH 7.0, while being gassed with air for 24 hours. After 24 hours, 200 ml of a solution of 10 g of nicotinic acid and 2.5 g of yeast extract in water and sterile was added and the fermentation was continued. After 42 hours, the culture was harvested and the Achromobacter cells were separated by centrifuging (30 min. at 15,000 g). 38.3 g of moist biomasses was obtained.

In a 7-liter fermenter, 2750 ml of a 2 percent nicotinic acid solution, which has been previously brought to pH 7.1 by addition of solid magnesium oxide, was inserted and was heated to 30° C. The hydroxylation began after the addition of 200 ml of concentrated suspension of the *Achromobacter xylosoxydans* DSM 2783 (final concentration $10^{10}$ cells/ml).

After the addition of antifoaming agent (for example, polypropylne glycol P-2000), the material in the fermenter was aerated while stirring strongly. The fermenter was thermostated to 30° C. The pH was held at pH 7.0 with the help of the pH stats and a solution of nicotinic acid as a correcting agent (total consuption 23 g). The substrate concentration was continuously measured with the conductive capacity measuring device. The latter was coupled with the peristaltic pump by way of a regulator. Whenever, in consequence of the formation and the precipitation of magnesium hydronicotinate, the substrate dropped, a supply solution of magnesium nicotinate (1M) was pumped to it until the original conductive capacity was reached again. Thus, it was possible to automatically control the substrate concentration. The crystals of magnesium hydronicotinate settled on the bottom of the fermenter vessel; they were taken out periodically, subjected to suction and the filtrate was returnd into the fermenter.

The installation was operated continuously for 3 days. 3 liters of 1 molar magnesium nicotinate solution was added. After the addition was completed, the reactor was operated for another 5 hours and then it was emptied. The suspension was subjected to suction. 5.3 l of filtrate and 650 g of moist magnesium or barium hydroxynicotinate were obtained.

The entire quantity of magnsium hydronicotinate was suspended in 2.5 l of water and was acidified with concentrated hydrochloric acid up to pH of 1.2. The 6-hydroxynicotinic acid obtained was subjected to suction. The crystals, which were still moist, were washed with 400 ml of water and were dried. 468.8 g of white, microcrystalline product was obtained which, accordingly to HPLC analysis contained 98.8 percent of 6-hydroxynicotinic acid. This corresponded to a yield of 91.6 percent, calculated on the nicotinic acid used.

EXAMPLE 2

In a 2.5 fermenter, 1 l of a 3 percent aqueous suspension of nicotinic acid was filled in and was brought to pH 7.0 by the addition of solid barium oxide. This substrate solution was thermostated to 30° C. After the addition of antifoaming agent (Rhodorsil 70414), 70 ml of a concentrated suspension ($OD^{550}nm=90$) of *Achromobacter xylosoxydans* DSM 2783 was introduced into the fermenter. The suspension was strongly aerated and stirred. The pH value was kept constant at 7.0 by the addition of solid nicotinic acid. The addition of substrate (1 molar solution of barium nicotinate) was automated, as in Example 1, by means of conductive capacity measurements and regulation.

After 2 to 3 hours, the concentration of barium hydroxynicotinate reached the saturation limit and the product began to crystallize. The crystals settled on the bottom of the fermenter and were removed periodically. The crystal slurry was subjected to suction and the filtrate was conducted back. The installation ran continuously for 60 hours. During the hydroxylation 1 l of 1 molar nicotinic acid (barium salt) was introduced into the fermenter. Additionally, another 6.8 g of solid nicotinic acid was used up for the pH control. The fermenter was emptied and the crystals of barium hydroxynitotinate adhering to the wall were scraped off. The suspsension was subjected to suction. 1.9 l of filtrate was obtained which, according to the HPLC analysis, contained 0.5 percent of nicotinic acid and 2.4 percent of 6-hydroxynicotinic acid. Th entire quantity of moist barium hydroxynicotinate was suspended in 200 ml of water. Concentrated hydrochloric acid was added to this until the pH droppd to pH 1.2. After 2 hours of stirring the 6-hydroxynicotinic acid was subjected to suction, was washed with 100 ml of water and was dried under vacuum at 50° C. 118.9 g of slightly yellow 6-hydroxynicotinic acid was obtained which, according to HPLC analysis, had a content of 98.3 percent. This corresponded to a yield of 64.7 percent, related to the nicotinic acid introduced into the system. When the analytically proven quantity of barium hydroxynicotinic acid remaining in the filtrate is included in the calculation, then the total yield is increased to 89.9 percent.

EXAMPLE 3

Production of the *Pseudomonas putida* NCIP 8176 biomasses.

A nutritional solution which contained 52 g of $Na_2HPO_4 \cdot 2H_2O$, 20 g of $KH_2PO_4$, 2.5 g of yeast extract and 10 g of nicotinic acid in 4750 ml of water was sterilized in a 7 l -Chemap fermenter for 20 min. at 120° C. After cooling to 30° C., 50 ml of sterile trace element solution was added so that the following final concentrations (in ml/l) was achieved:
CaCl$_2$.2H$_2$O: 20
MnSO$_4$: 10
FeSO$_4$.7H$_2$O: 5
CoCl$_2$.6H$_2$O: 0.1
CuSO$_4$.5H$_2$O: 0.1
ZnSO$_4$.7H$_{d2}$O: 0.1
NaMoO$_4$.2H$_2$O: 0.1

The fermenter was inoculated with 500 ml of Pseudomonas starter culture and was fermented at 30° C. and pH 7.0, while gassing it with air for 24 hours. After 24 hours, 200 ml of sterile solution of 10 g of nicotinic acid and 2.5 g of yeast extract in water was added and the fermentation was continued. After 38 hours, the cell mass was separated by centrifuging (30 min. at 10,000 g). 43.3 g of moist biomass was obtained.

Hydroxylation of the nicotinic acid

In a 3.5 l fermenter, 2 l of a 0.5 percent nicotinic acid solution was brought to pH 7.0 by the addition of solid magnesium oxid and was heated up to 30° C. The hydroxylation began after the addition of 20 g of moist *Pseudomonas putida* NCIB 8176 biomass which previously was suspended in 100 ml of water. At the same time, an antifoaming agent (polypropylene glycol P-2000 Fluka) was added and air was introduced into the mixture so that the concentration of the dissolved oxygen remained in the range of 3 to 5 mg O$_2$/l. The pH was kept at pH 7.0 through the addition of nicotinic acid as a correcting agent (total consumption was 15.2 g). The substrate concentration was kept constant by a controlled addition of 1 molar Mg-nicotinate with the help of a conductive capacity measurement and regulation (see Example 1).

After reaching the saturation concentration, the magnesium salt of the 6-hydroxynicotinic acid began to precipitate. The crystals which settled on the bottom of the fermenter were removed periodically and subjected to suction. The filtrate which was obtained in each case was used for the production of a 1 molar magnesium nicotinate solution. The crystals were stored in a moist state. The speed of the addition of the educt (1 molar solution of magnesium nicotinate) was measured and used for the determination of the total enzyme activity in the fermenter. Losses of activity were compensated by periodic additions (once a day) of fresh, moist biomass. The experimental series lasted 5 days. During this time, 1.6 l of 1 molar magnesium nicotinate was introduced into the fermenter. For the determination of the yield, the fermenter was emptied and the crystals adhering to the wall were scraped off. Th crystals were subjected to suction. The Mg-hydroxynictinate obtained in the entire series of experiments was suspended in 1.5 l of water and was slowly brought to a pH of 1.5 by the addition of concentrated hydrochloric acid. The crystals of the 6-hydroxynicotinic acid were subjected to suction on the suction strainer, were washed with 200 ml of water and were dried at 60° C. under vacuum. 365.0 g of white crystals were obtained which, according to HPLC analysis, had a content of 99.3 percent. This corresspondd to a yield of 92.4 percent, related to the nicotinic acid introduced into the fermenter.

What is claimed is:

1. Process for the production of 6-hydroxynicotinic acid, comprising (a) directly enzymatically hydroxylating nicotinic acid by a microorganism in a nutritive culture medium in the course of fermentation in the presence of (i) a chemically equivalent quantity of magnesium ions or barium ions, and (ii) an aqueous medium, the microorgaism being a nicotinic acid-hydroxylating microorgaism which is selected from the group consisting of a Bacillus species microorganism, a Pseudomonas species microorganism and an Achromobacter species microorganism, such components forming a reaction mixture, (b) separating the resultant magnesium or barium salt of the 6-hydroxynicotinic acid from the reaction mixture, and (c) chemically separating the 6-hydroxynicotinic acid from the separated salts.

2. The process as claimed in claim 1 wherein a saturated solution of magnesium ions or barium ions of the nicotinic acid, the latter being inserted continuously into a suspension of an *Achromobacter xylosoxydans* held at pH of 5 to 9 according to the measure of the enzymatic hydroxylation to the corresponding 6-hydronicotinic acid, and continuously separating the resultant salts of 6-hydroxynicotinic acid.

3. The process as claimed in claim 2 wherein the process is operated at a temperature of 10° to 50° C.

4. The process as claimed in claim 3 wherein the pH is held constantly at 5 to 9 by the addition of nicotinic acid.

5. The process as claimed in claim 1 wherein the microorganism is *Achromobacter xylosoxydans* of the designation DSM 2783.

6. The process as claimed in claim 1 wherein the process is operated at a temperature of 10° to 50° C.

7. The process as claimed in claim 1 wherein the pH is held constantly at 5 to 9 by the addition of nicotinic acid.

8. The process as claimed in claim 1 wherein the reaction is carried out continuously.

9. The process as claimed in claim 1 wherein the microorganism is *Achromobacter xylosoxydans* of the designation DSM 2783.

* * * * *